US006979726B1

(12) United States Patent
von Hoegen et al.

(10) Patent No.: US 6,979,726 B1
(45) Date of Patent: Dec. 27, 2005

(54) IMMUNOCONJUGATES

(75) Inventors: Ilka von Hoegen, Doffenheim (DE); Uwe Hofmann, Alsbach (DE); Carlota-Silvia Jaggle, Darmstadt (DE); Wolfgang Strittmatter, Ober-Ramstadt (DE); Jörg Stadlmüller, Seeheim (DE); Siegfried Matzku, Zwingenberg (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 08/362,951

(22) Filed: Dec. 23, 1994

(30) Foreign Application Priority Data

Dec. 24, 1993 (EP) .................................. 93120865

(51) Int. Cl.⁷ ............................................ C07K 16/00
(52) U.S. Cl. ................................ 530/387.1; 530/387.7
(58) Field of Search ........... 530/391.7; 435/69.7–71.1; 424/178.1

(56) References Cited

U.S. PATENT DOCUMENTS 5,314,995 A * 5/1994 Fell, Jr. et al.
5,470,571 A * 11/1995 Herlyn et al. .............. 424/1.49

FOREIGN PATENT DOCUMENTS

| AU | 53795 | * 12/1990 |
| EP | 0 396 387 | 11/1990 |
| EP | 0 439 095 | 7/1991 |
| EP | 0 586 002 | 3/1994 |
| WO | 91/03489 | 3/1991 |
| WO | 95/08495 | 5/1992 |
| WO | 92/15683 | 9/1992 |
| WO | 93/00917 | 1/1993 |
| WO | 95/25167 | 9/1995 |

OTHER PUBLICATIONS

Morrison SL Hospital Practice Oct. 15, 1989 pp 65-80.*
John Mendelsohn, Monographs (National Center Inst.) No. 15 pp. 125-131, 1992.*
Adachi K et al (J. Nippon Medical School Oct. 1991, 58 (5) 537-46, abstract only.*
Lappin MB et al Blood Reviews 2000;14:228-239.*
Naramura et al (Immunol Lett. Dec. 1993; 39(1):91-9).*
Mendelsohn, John, "Growth Factor Receptors as Targets for Antitumor Therapy with Monoclonal Antibodies", *Monoclonal Antibody Therapy Prog. Allergy*, Basel, Karger, 1988, vol. 45, pp. 147-160.
*Chemical Abstracts*, vol. 120, No. 21, May 23, 1994.
U.P. Shinde et al., "Protein memory through altered folding mediated by intramolecular chaperones", *Nature*, vol. 389, pp. 520.522, Oct. 1987.
Philip J. Bassford et al., "Use of Gene Fusion to Study Secretion of Maltose-Binding Protein into *Escherichia coli* Periplasm", *J. of Bacteriology*, 139(1): Jul. 19-31, 1979.
DIALOG Abstract, Winther et al., "Propetide of carboxypeptidase Y provides a chaperone-like function as well as inhibition of the enzymatic activity", *Proc. Natl. Acad. Sci. USA*, 88(20):9330-4, Oct. 1991.

* cited by examiner

*Primary Examiner*—Jeffrey Siew
*Assistant Examiner*—C. Yaen
(74) *Attorney, Agent, or Firm*—Millen, White, Zelano, Branigan, P.C.

(57) ABSTRACT

The present invention relates to new fusion proteins which consist of a tumor-associated targeting element preferentially a monoclonal antibody or a fragment thereof recognizing a molecule which is preferentially expressed on human tumor cells such as the human epidermal growth factor receptor (EGFR), and a biologically active ligand such as a growth and/or differentiation factor. The resulting fusion protein may be used to deliver the biologically active ligand to a specific target cell or tissue. The new immunoconjugates can be used in tumor therapy.

3 Claims, 6 Drawing Sheets

IMMUNOCONJUGATES

Figure 1A:
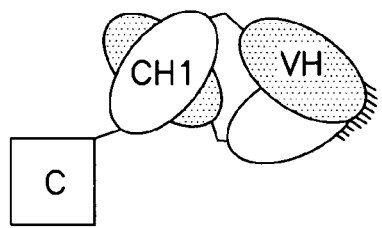

The present invention relates to new fusion proteins which consist of a tumor-associated targeting element preferentially a monoclonal antibody or a fragment thereof recognizing a molecule which is preferentially expressed on human tumor cells such as the human epidermal growth factor receptor (EGFR), and a biologically active ligand such as a growth and/or differentiation factor. The resulting fusion protein may be used to deliver the biologically active ligand to a specific target cell or tissue. The new immunoconjugates can be used in tumor therapy.

BACKGROUND OF THE INVENTION

A variety of different therapeutic concepts have been used for the treatment of cancer patients. In the past years clinical trials have been performed with monoclonal antibodies, which recognize specifically or preferentially cell surface molecules expressed on malignant cells. Aim of this approach is the induction of antibody-dependent cellular cytotoxicity (ADCC) or complement-mediated cytotoxicity (CDC) to eliminate tumor cells. A second approach is the cytokine-mediated activation of an immune response. The cytokine-induced anti-tumor activity can be mediated by:
1) a direct cytotoxic/cytostatic effect of the cytokine on tumor growth
2) tumor-antigen-nonspecific mechanisms such as LAK activity or monocyte/macrophage mediated cytotoxicity
3) tumor-antigen specific immune responses mediated by CD4 and CD8-positive T cells. In this situation a systemic immunity against the tumor has been observed in animal models.

Unfortunately, systemic application of cytokines such as IL-2 or TNFα is hampered by their toxicity (Rubin, Cancer Invest. 11:460–472, 1990; Balkwill, Nature 361:206–207, 1993). To ensure a sufficient cytokine concentration at the tumor site rather high doses have to be administered and the maximumly tolerable dose is below the dose required for efficacy. Therefore, the negative effects of cytokines are mainly a consequence of the systemic application, but their clinical relevance in tumor therapy is undoubted. In animal models it was demonstrated that in situ presence of the cytokine either by intratumoral injection or by secretion of transfected tumor cells may lead to tumor regression (Hock et al. PNAS 90:2774–2778, 1993; Colombo et al. Cancer Res. 52:4853–4857, 1992; McBride et al., Cancer Res. 52:3931–3937, 1992; Tepper et al., Science 257:548–551, 1992; Mullen et al., Cancer Res. 52:6020–6024, 1992; Blankenstein et al., J. Exp. Med 173:1047–1052,1991; Gansbacher et al., J. Exp. Med. 172:1217–1224, 1990). In these systems, cytokines do not impair tumor proliferation, but are capable of activating a rapid and potent anti-tumor reaction. Therefore, the physical combination of an effector molecule and a targeting element represents a means of reducing the peripheral presence and enhance the intratumoral availability of the biologically active ligand. Furthermore, single tumor cells or micro-metastases can also be targeted by these molecules.

The biologically active ligand for an antibody-directed targeting should induce the destruction of the target cell either directly or through creating an environment lethal to the target cell. The biologically active ligand can be a cytokine such as IL-1, IL-2, IL-4, IL-6, IL-7, IL-10, IL-13, IFNs, TNFα or CSFs. These cytokines have been shown to elicit anti-tumor effects either directly or by activating host defense mechanisms (Mire-Sluis, TIBTECH 11:74–77,1993; Colombo et al. Cancer Res. 52:4853–4857, 1992; Thomas & Balkwill, Pharmac. Ther. 52:307–330, 1991).

For instance, IL-2 is considered the central mediator of the immune response. Il-2 has been shown to stimulated the proliferation of T cells and NK cells and to induce lymphokine-activated killer cells-(LAK). Tumor-infiltrating T lymphocytes proliferate in response to IL-2. Furthermore, Il-2 enhances the cytotoxicity of T cells and monocytes. In addition, IL-2 induces a cytokine cascade secreted by T cells, NK cells and monocytes which further potentiate the immune response.

TNFα has found a wide application in tumor therapy, mainly due to its direct cytotoxicity for certain tumor cells and the induction of hemorrhagic regression of tumors. In addition, TNFα potentiates the immune reponse: it is a costimulant of T cell proliferation, it induces expression of MHC class I and class II antigens and TNFα, IFN and IL-1 secretion by macrophages. IL-4 was initially described as a B cell growth factor. In further studies IL-4 was shown to stimulate antigen-specific cytotoxic T cells and to act specifically on T cell-like LAK cells rather than NK cell like LAK cells. IL-4 inhibits the growth of human melanoma cells enhances their MHC class I and II expression. The induction of macrophage mediated anti-tumor effects by IL-4 is still controversial.

IL-7 is a growth factor for pre-B cells as well as for human peripheral CD4 and CD8 positive T cells. IL-7 directly augments the cytotoxicity of the CD8-positive T cell subpopulation. In addition IL-7 induces the production of IL-1, IL-6 and TNFα by peripheral monocytes. In vitro, the tumoricidal activity of monocytes/macrophages can be stimulated by IL-7, possibly mediated by cytokines, such as TNFα.

Epidermal growth factor (EGF) is a polypeptide hormone which is mitogenic for epidermal and epithelial cells. When EGF interacts with sensitive cells, it binds to membrane receptors (EGFR). The EGFR is a transmembrane glycoprotein of about 170 kD, and is a gene product of the c-erb-B proto-oncogene.

The murine monoclonal antibody MAb 425 was raised against the human A431 carcinoma cell line (ATCC CRL 1555) and found to bind to a polypeptide epitope on the external domain of the EGFR. It was found to inhibit the binding of EGF and to mediate tumor cytotoxicity in vitro and to suppress tumor cell growth of epidermal and colorectal carcinoma-derived cell lines in vitro (Rodeck et al., 1987, Cancer Res. 47, 3692). Humanized and chimeric versions of MAb 425 are known from WO 92/15683.

Antibody-cytokine immunoconjugates in various combinations for the directed delivery of active proteins have been described previously. IL-2 was combined with the human carcinoma-specific antibody L6 (Fell et al., 1991, J. Immunol. 146:2446–2452, EP-OS-0439095), or with an anti-ganglioside GD2 antibody (Gillies et al., 1992, PNAS 89:1428–1432, WO 92/08495). Immunoconjugates comprising of an anti-dansyl antibody and IGF1 have been generated for the directed delivery of hormones (Shin & Morrison, 1990, PNAS 87:5322–5326, WO 91/14438).

Thus, it was object of the invention, to create antibodies or fragments thereof comprising (1) an epitope directed to an EGFR antigen on the surface of a tumor cell and (2) a biologically active ligand having a high potential for induction of cytotoxicity, and, therefore, intensifying the anti-tumor effect in situ.

SUMMARY OF THE INVENTION

Figure 1B:
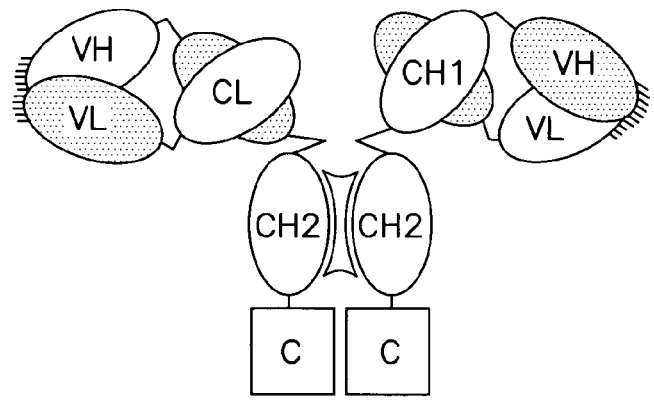
Figure 1C:
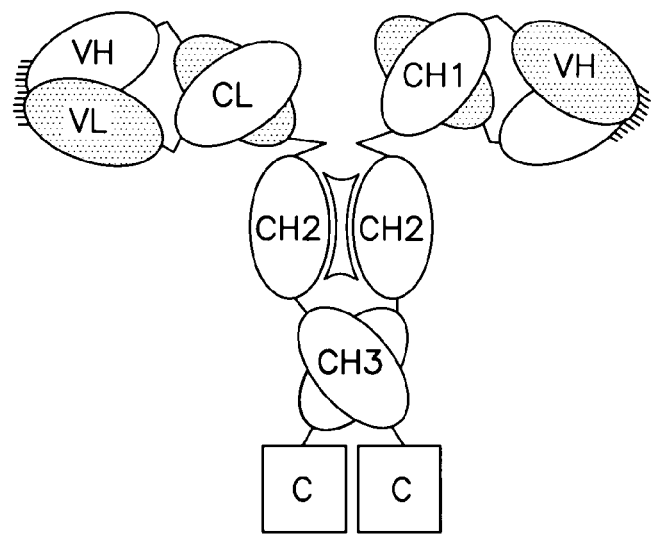

The invention relates to immunoconjugates which combine part of a monoclonal antibody minimumly the antigen-recognition site or a complete monoclonal antibody with a biologically active ligand. The constructs encoding these immunoconjugates can be generated with recombinant DNA technology methods. The immunoconjugates can contain the variable region of the antibody heavy chain and the CH1 domain of the constant region (antibody-CH1 conjugate), or the CH1 and CH2 domain of the constant region (antibody-CH2 conjugate), or the CH1, CH2 and CH3 domain of the constant region (antibody-CH3 conjugate) fused to the biologically active ligand. By addition of the appropriate light chain immunoconjugates can be generated which target antigen-bearing cells and deliver an active ligand to a specific site in the body (FIG. 1 a–c).

By means of the immunoconjugates according to the invention, e.g., tumors, such as melanoma, glioma and carcinoma can be detected and treated successfully.

Thus, it is an object of the present invention to provide an immunoconjugate comprising of (1) a monoclonal antibody or a fragment thereof directed to a tumor cell bearing an antigen epitope of the epidermal growth factor receptor (EGFR), and (2) a biologically active ligand, preferably a cytokine, which is fused to said antibody or antibody fragment and having a capacity of a tumor-specific cytotoxic immune response which induces the lysis and death of the tumor cell. Proteins with direct cytotoxic activity can also be used according to the present invention, e.g., toxin, such as Pseudomonas exotoxin. Further examples for suitable ligands are given in J. Drug Targeting 1994, Vol. 2, 183–215 (G. A. Pietersz, K. Krauer). A cytokine is, e.g., a class of soluble protein or polypeptide mediators which take part in the regulation of the immune system.

A cytokine can be, e.g., TGF-$\beta$1, TGF-$\beta$1.2, TGF-$\beta$2, TGF-$\beta$3, TGF-$\beta$5M, LAP TGF-$\alpha$, TGF-$\beta$, sRII, sTNF RI, sTNF RI, sTNF RII, TNF-$\beta$, PDGF, PDGF-AA, PDGF-BB, PDGF-AB, HGF, VEGF, $\beta$-NGF, EGF, IGF-I, IGF-II, HB-EGF, FGFa, FGFb, FGF-4, FGF-5, FGF-6, KGF, SLPI, PTN, IFN-$\tau$, $\beta$-ECGF, ANG, OSM, PD-ECGF, ENA-78, IL-1$\alpha$, IL-1$\beta$, IL-3, IL-5, IL-6, IL-8, IL-9, IL-10, IL-11, IL-12, IL-13, IL6 sR, IL-1ra, gp130, IL4 sR, IL-1 sRII, IL-5 sR, M-CSF, GM-CSF, G-CSF, EPO, LIF, SCF.

An antibody according to the present invention is preferably a monoclonal which (1) binds the external EGF-R domain; and (2) competes with EGF binding. In a preferred embodiment according to the invention, the antibody or antibody fragment derives from murine, humanized or chimeric MAb 425.

In a further preferred embodiment of the invention, the immunoconjugate is selected from the group MAb 425-CH1-TNF$\alpha$, MAb 425-CH2-TNF$\alpha$, MAb 425-CH3-TNF$\alpha$, MAb 425-CH1-IL2, MAb 425-CH2-IL2 and MAB 425-CH3-IL2, MAb 425-CH1-II-7, MAb 425-CH2-II-7 and MAb 425-CH3-II-7. Furthermore, it is an object of the invention to provide a method for manufacturing an immunoconjugate as defined above and in the claims by means of a host organism by fusing the DNA sequences encoding for the antibody or antibody fragment and the biologically active ligand with one another, placing the resulting construct into an expression vector which is transformed into said host organism, cultivating the host cells in a nutrient solution, expressing the fusion protein. The fusion protein can be isolated by conventional methodology, e.g., by affinity chromatography, or used directly as a supernatant obtained from cultures.

In a preferred embodiment according to the invention, a technology is used wherein the DNA sequences encoding for the antibody or antibody fragments and the biologically active ligand are fused on a single stranded DNA by means of a oligonucleotide which is complementary to the desired fusion DNA-sequence.

Furthermore, it is an object of the invention to provide a pharmaceutical composition comprising at least an immunoconjugate as defined above and in the claims and a physiologically acceptable carrier.

Finally, it is an object of the invention the use of the immunoconjugates as defined above and in the claims for the preparation of a drug directed to tumors and its use therefore to treat tumors. The immunoconjugates according to the present invention can be administered analogously, e.g., to the method disclosed in Riethmueller et al., 1994, The Lancet, 343, 1177–1183: "Randomized trial of monoclonal antibody for adjuvant therapy of resected DukesC colorectal carcinoma".

It was found that especially in the case of the antibody-CH2 and antibody-CH 3 conjugates such as, for example, MAb 425-CH2-TNF$\alpha$ and MAb 425 -CH3-TNF$\alpha$ the induction of cellular cytotoxicity was superior as compared to uncoupled TNF$\alpha$. While not bound by any theory, this can be due to the combination regarding the binding properties and the induction of ADCC by the constant regions of the monoclonal antibody and the cytokine activities.

The antibody-CH1 conjugates according to this invention are advantageous with respect to the small molecular size and the possibility of expression in prokaryotes. Furthermore, the small size will facilitate (tumor) tissue penetration.

The immunoconjugates of the invention show additionally good binding and proliferation properties in comparison with the monoclonal antibody, preferably MAb 425, as such, or fragments thereof.

The immunoconjugates can also be used, e.g., to eliminate EGF-R expressing cell types from cultures of mixed cells to prepare populations of homogeneous cells. Such homogeneous cell populations can be used for commercial research tool purposes to study, e.g., cytotoxic or immune response or to obtain components of said cells in more purified form, e.g., absent the EGF-R.

Monoclonal Antibodies

MAb 425 is an IgG1 murine monoclonal antibody raised against the human A431 carcinoma cell line (ATCC CRL 1555). MAb 425 binds to a polypeptide epitope of the external domain of the human EGF receptor and competes with the binding of EGF. MAb 425 was found to mediate tumor cytotoxicity in vitro and to suppress tumor cell growth of epidermoid and colorectal carcinoma derived cell lines in vitro (Rodeck et al., 1987, Cancer Res. 47:3692). Humanized and chimeric versions of MAb 425 have been disclosed in WO 92/15683. MAb 425 or an antibody having such characteristics, can be obtained as disclosed in the above-mentioned references.

Cytokines

Cytokine-encoding cDNAs were either purchased from British Biotechnology Limited (Herrmann Biermann GMBH, Bad Nauheim FRG: human IL-2 BBG30, human IL-4 BBG15, human IL-7 BBG43, human TNF$\alpha$ BBG18). The commercially available cDNAs are lacking the signal sequence necessary for protein excretion. Cytokine-encoding cDNAs can be generated from mRNA isolated from cytokine-producing cells.

Vectors pUC19 is part of a series of related high copy number *E. coli* plasmid cloning vectors and contains portions of pBR322 and M13 mp19. pUC19 contains the inducible bacterial lac promoter-operator, followed by a multiple cloning site (Yanisch-Perron et al., Gene 33:103–109,1985). pUC vectors are commercially available (e.g. New England Biolabs). The pBluescript KS/SK+ and KS/SK− phagemid vectors are derived from pUC19. The vectors are commercially available (Stratagene).

The eucaryotic expression vector pHCMV (Gillies et al., 1983, Cell 33:717) contains the origin of replication of the simian virus 40 (SV40) and the promotor and enhancer region of the human cytomegalovirus. The promotor/enhancer region is followed by a multi cloning site (mcs) for the introduction of genes to be expressed. In this vector the chimeric form of the mAB425 heavy chain variable region and the ΔSacII cγ1 region fused with the effector molecule at the end of the CH1, CH2 or CH3 domain, respectively, were combined to generate a MAb 425 heavy chain fusion protein. The fusion Ig chain can be assembled into the immunoconjugate by combining it with the appropriate light chain to form a monovalent antigen-binding region, which can then be associated to produce a divalent immunoconjugate specific for the target antigen (FIG. 1). The heavy and light chain constructs can be placed in the same or separate vectors.

The procaryotic expression vector is based on the pSW1 vector (Ward et al., Nature 341: 544–546, 1989), which is a derivative of the pUC19 vector. pSW1 contains a sequence coding for the leader peptide of the bacterial pelB gene from *Erwinia carotovora* (Lei et al., J. Bact. 169:4379–4383, 1987). Foreign DNAs can be introduced in frame behind the pelB leader sequence to direct protein expression into the periplasm.

BRIEF DESCRIPTION OF THE FIGURES AND TABLES

Figure 2:
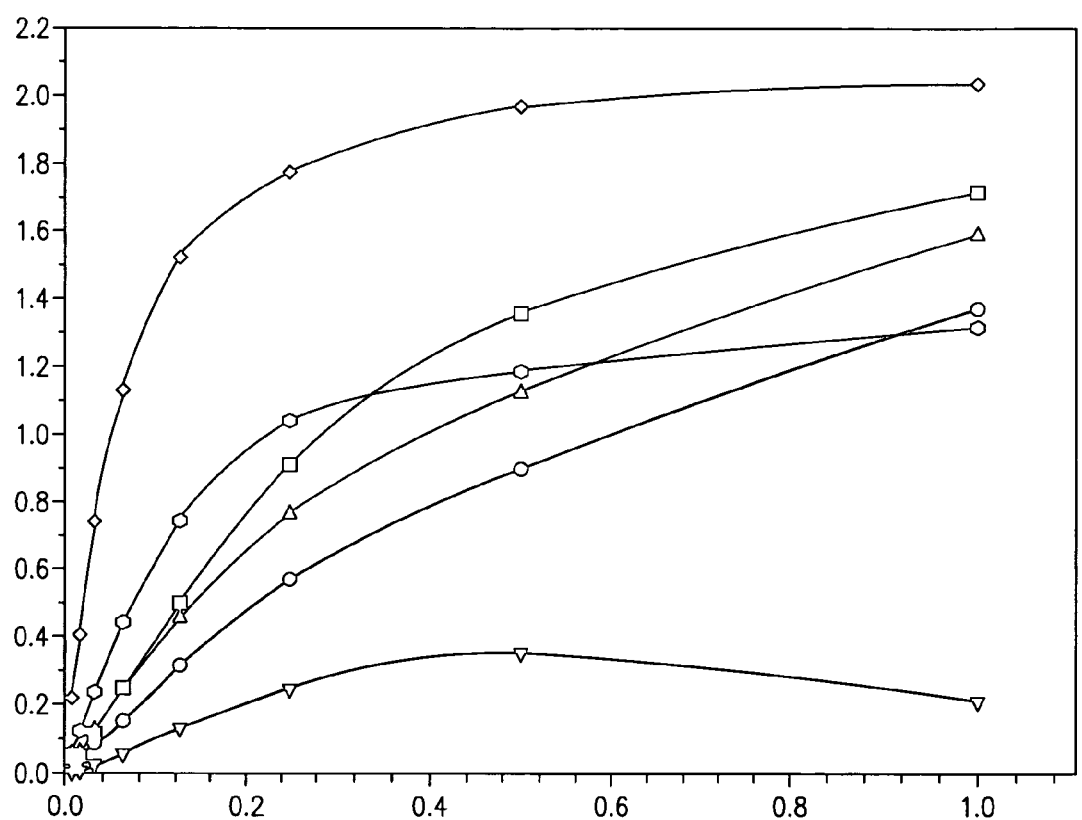

Table 1: PCR primers used for the generation of MAb425-cytokine fusion proteins (eucaryotic expression)
Reverse primer hybridizing to the Stratagene pBluescript vectors SK+/−and KS+/−(commercially available);
This primer hybridizes to the Cg1 constant region including the unique SacII site;
Reverse primer hybridizing to M13 derived vectors (commercially available).
Table II: PCR primers used for the generation of MAb425-cytokine fusion proteins (procaryotic expression)
FIG. 1: Model of antibody-cytokine Immunoconjugates.
C=cytokine; VH=heavy chain variable region; VL=light chain variable region; CH=constant region heavy chain; CL=constant region light chain.
(a) antibody-CH1 conjugate, (b) antibody-CH2 conjugate, (c) antibody-CH3 conjugate.
FIG. 2: Binding of Immunoconjugates to EGF-R In an EGF-R-specific ELISA.
Supernatants of transiently transfected COS-7 cells were tested for immunoconjugate content. Vertical axis: % absorbance at 490 nm; horizontal axis: Dilution of supernatant (log2). MAb425CH1-TNFα (filled circles), MAb425CH2-TNFα (filled squares), MAb425CH3-TNFα (filled triangles), MAb425-control (filled diamond), MAb425Fab-control (inverted filled triangle), MAb425F(ab')₂ reshaped (purified protein) (filled hexagon).

Figure 3A:
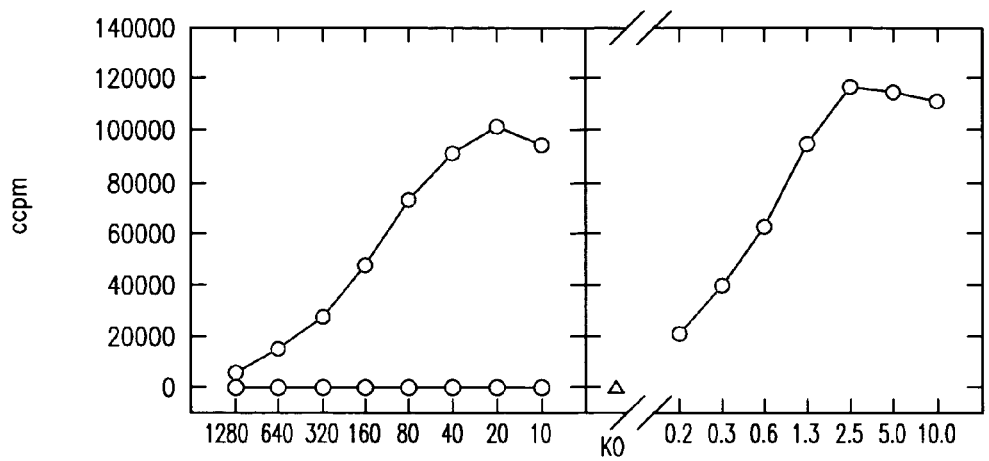
Figure 3B:
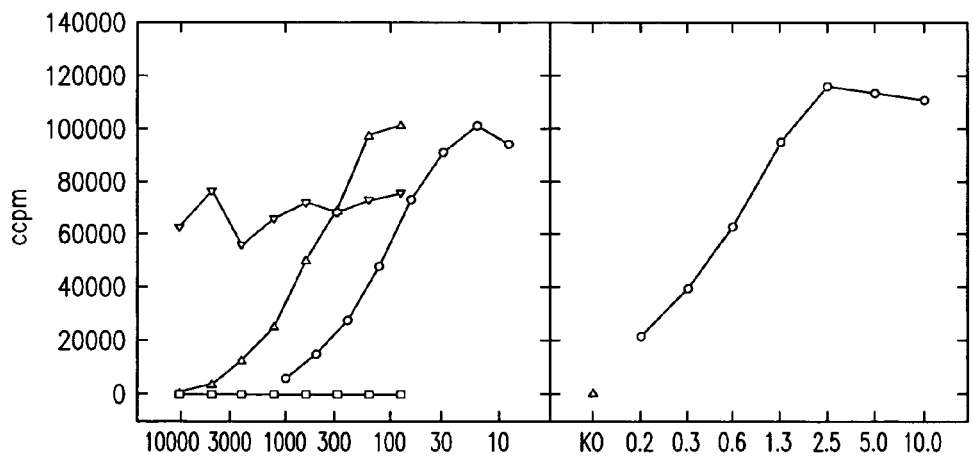
Figure 3C:
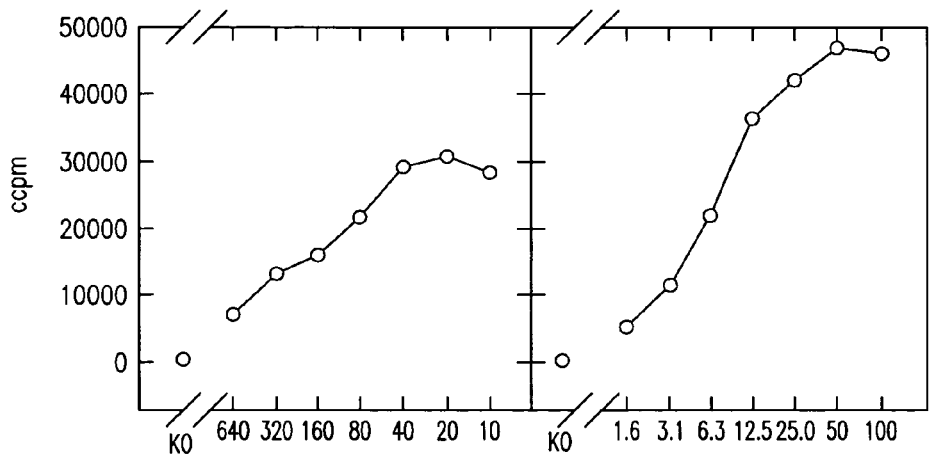

FIG. 3A: IL-2 activity of MAb425-CH1-IL-2 immunoconjugate expressed in COS-7 cells.
CTLL-2 cells were used as indicator cell line. Proliferative activity of serially diluted COS supernatant containing MAb425-CH1—IL-2 is shown in the left panel (filled circles). COS supernatant containing MAb425Fab-control were used as control (open circles). Filled triangel: medium control. Proliferative response of CTLL.2 cells upon activation with recombinant commercial IL-2 protein or without IL-2 (KO) is given in the right panel.
Left panel: horizontal axis=reciprocal dilution, vertical axis: radioactivity (ccpm)
Right panel: horizontal axis=IL-2 (U/lml), vertical axis: radioactivity (ccpm)
FIG. 3B: IL-2 activity of MAb425-CH1-IL-2 immunoconjugate expressed in *E. coli*.
CTLL-2 cells were used as indicator cell line. Left panel: Proliferative activity of serially diluted MAb425-CH1-IL-2 expressed in *E. coli* and affinity purified over an anti-MAb425 idiotypic column is shown in the left panel (filled triangles). COS supernatant containing MAb425-CH1-IL-2 were used as control (closed circles). Dialysis buffer (closed squares). To ensure that the buffer did not affect IL-2 activity, dialysis buffer was titrated in the presence of a constant concentration of IL-2 (1 U/ml) (inverted filled triangles). Right panel: Proliferative response of CTLL.2 cells upon activation with recombinant commercial IL-2 protein (closed circles) or without IL-2 (KO) (closed triangle).
Left panel: horizontal axis=reciprocal dilution, vertical axis: radioactivity (ccpm)
Right panel: horizontal axis=IL-2 (U/lml), vertical axis: radioactivity (ccpm)
FIG. 3C: Induction of TIL proliferation by MAb425-CH1-IL-2 immunoconjugate.
Melanoma tumor infiltrating (TIL) lymphocytes were cultured without (KO) or in the presence of serially diluted COS supernatants containing 425-CH1-IL-2 immunoconjugate (left panel). Proliferative response of TILs upon activation with recombinant commercial IL-2 is shown in the right panel.
Left panel: horizontal axis=reciprocal dilution, vertical axis: radioactivity (ccpm)
Right panel: horizontal axis=IL-2 (U/lml), vertical axis: radioactivity (ccpm)
FIG. 4: Induction of HPBL proliferation by MAb425-IL-4 immunoconjugates (human peripheral blood lymphocytes)
PHA-activated HPBLs were cultured in the presence of serially diluted COS-supernatants containing MAb425-CH2-IL-4 (closed circles), MAb425-CH3-IL-4 (closed triangles) fusion proteins. Supernatants containing MAb425 (closed square), IL-4 (closed diamond) and vector control (closed inverted triangle) were used as control. Proliferative response of HPBLs upon activation with recombinant commercial IL-4 and without growth factor (KO) is shown in the right panel. Upper Panel: horizontal axis=IL-4 (U/ml), lower panel: horiz. axis=dilution, vertical axis: radioactivity (ccpm)
FIG. 5: MAb425-TNFα immunoconjugate cytotoxicity on WEHI 164 cells.
TNFα sensitive murine fibrosarcoma cell line WEHI 164 were cultured for 48h in the presence of serially diluted COS supernatants (left panel) containing 425-CH1-TNFα immunoconjugate (filled squares) or 425-CH2-TNFα immunoconjugate (filled triangles) or MAb425Fab-control (filled circles). Growth inhibition of indicator cells induced by commercial recombinant human TNFα is given in the right panel. Horizontal axis: dilution (upper panel), TNFα (U/ml) (lower panel).

Figure 6:
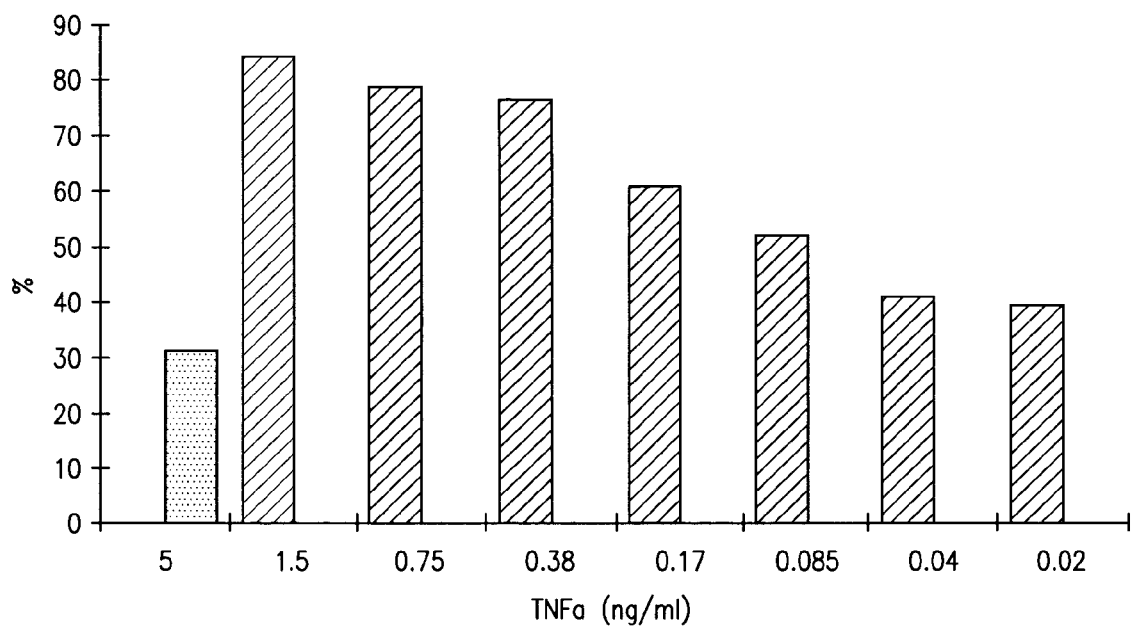

FIG. 6: MAb425-TNFα immunoconjugate mediated tumor cytolysis by PBMC.

Non-activated human peripheral blood lymphocyte (PBMC) were used as effector cells and cocultured with allogeneic EGF-R-positive $^{51}$Cr-labeled C8161 target cells at an effector/target ratio of 30:1. Percent specific lysis is given after 18h of coculture without or in the presence of serially diluted COS-supernatant containing MAb 425CH3-TNFα immunoconjugate (hatched bars). Recombinant TNFα (Genzyme) was expressed as a 36 kDa dimer in *E. coli* (dotted bars). Vertical axis: % specificy lysis.

DETAILED DESCRIPTION OF THE INVENTION

General:

Other microorganisms, cell lines, plasmids, promoters, resistance markers, replication origins, restriction sites or other fragments of vectors which are mentioned in the application are commercially or otherwise generally available. Provided that no other hints are given, they are used only as examples and are not essential according to the invention and can be replaced by other suitable tools and biological materials, respectively.

Expression of Fusion Proteins in Eucaryotic Cells

Construction of the Eukaryotic Expression Vectors for Fab425-Cytokine Fusionprotein Expression Fusion of MAb425 and Cytokines by Loop-Out Technology:

Generation of TNFα Constructs:

The SacII/XbaI fragment of the ΔSacII cγ1 clone was inserted into Bluescript SK+ containing the cytokine-encoding sequences such as the TNFα cDNA. The TNFα cDNA was introduced between the SmaI and EcoRI site. The resulting construct was prepared as single stranded DNA by addition of the appropriate helper phage. The CH2 or CH3 domain was fused in frame to the 5' end of the TNFα coding sequence. The oligo-nucleotides

```
5' CGAAGATGATCTGACCAT TTTGGCTTTGGAGATGGT 3'
        TNFα        |    cγ1 CH2 domain 5' CGAAGATGATCTGACCAT TTTACCCGGAGACAGGGA 3'
        TNFα        |    cγ1 CH3 domain
``` are homologous to the 3' end of the CH2 domain and CH3 domain, respectively, and the 5' end of the TNFα coding sequence. The single stranded DNA sequences are held together by the oligonucleotide and the unwanted sequences between are removed from the construct. The oligonucleotides have the opposite orientation, because the upper strand was generated as single stranded DNA.

The DNA was filled up to the double-stranded form by sequenase polymerase. This enzyme is not error-prone like Amplitaq DNA polymerase and therefore only the DNA sequence of the junction of isolated clones was determined. Those clones with the correct sequence were combined with the sequences necessary to generate a complete mAb425 fusion protein and cloned into the pHCMV vector for expression in eucaryotic cells.

Generation of IL-4 Constructs:

For these constructs the complete ΔSacII cγ1 clone was inserted into Bluescript KS+ as KpnI/SalI fragment. IL-4 was cloned as HindIII/EcoRI fragment into the same vector. The fusion was performed as described for the TNFα constructs with the oligonucleotides

```
5' GATATCGCACTTGTGCAT TTTGGCTTTGGAGATGGT 3'
        IL-4        |    cγ1 CH2 domain 5' GATATCGCACTTGTGCAT TTTACCCGGAGACAGGGA 3'
        IL-4        |    cγ1 CH3 domain
``` for the fusion to the CH2 and CH3 domain, respectively.

The clones with the correct sequence were combined with the sequences necessary to generate a complete mAb425 fusion protein and cloned into the pHCMV vector for expression in eucaryotic cells.

Fusion of MAb425 and Cytokines by PCR Technology

Amplitaq DNA polymerase is error prone and to ensure that no errors were incorporated the sequences of those segments amplified by PCR technology was determined. Primers used in these experiments are summarized in Table I.

Generation of CH1 Fusion Proteins

The pUH5 plasmid contains the sequences for the heavy chain FAb425 fragment for procaryotic expression with the N-terminal pelB leader-sequence derived from *Erwinia carotovora* (Lei et al., J. Bact. 169:4379–4383,1987) to ensure protein secretion. The HindIII/NotI fragment was recloned into the bluescript KS+ vector. The cytokines IL-4 and IL-7 were amplified by PCR technology to introduce a 5' NcoI and a 3' BamHI restriction site, respectively. IL-2 and TNFα already contain the 5' NcoI and 3' BamHI restriction sites. All cytokines were cloned as NcoI/BamHI fragments behind the CH1 domain. In these constructs the cytokine sequences were not in frame. Therefore an adaptor (5'TCGACMGAAAG 3') was introduced between the SalI and NcoI restriction sites. In the resulting constructs the heavy chain and the cytokine are expressed as a fusion protein with one additional amino acid (Ala) introduced by the adaptor sequence. The DraIII/BamHI fragments were cloned into the pHCMV expression vector containing the complete MAb425 heavy chain cDNA clone. In this construct the pelB leader sequence was exchanged with the leader sequence of the MAb425 heavy chain cDNA.

Generation of CH2 and CH3 fusion proteins

The ΔSacII cγ1 DNA was amplified by PCR technology, in two separate reactions using CH2-3'end primers which overlap, in frame, with the 5'end of the corresponding cytokine such as IL-2 and IL-7. The IL-2 and IL-7 cDNA clones were also amplified by PCR. At the 3'end unique NotI and SalI site were incorporated into the IL-2 construct and an unique XbaI site into the IL-7 construct to facilitate subcloning into the SK+ vector and subsequently into the pHCMV expression vector. The fusion of the IL-2 and IL-7 PCR products with the complete ΔSacII cγ1 region was done by PCR recombination. The resulting BamHI/NotI ΔSacII cγ1 CH2-IL-2 fragment was subcloned into SK+ containing the mAb425 heavy chain variable region. The SacII/XbaI ΔSacII cγ1CH-2 IL-7 fragment was subcloned into the SK+ vector containing mAb425 heavy chain variable region and the ΔSacII cγ1 region up to the SacII site. This procedure generated the complete mAb425-CH2 IL-2 and IL7 fusion genes, respectively. The complete mAb425-CH3 IL-2 fusion gene was generated accordingly with the exception that the ΔSacII cγ1 was amplified from the unique SacII site as the 5'end. The SacII/PstI fragment of the mAb425-CH2 IL-2 in SK+ containing the CH2 IL-2 fusion was then exchanged with the SaII/PstI fragment containing the CH3 IL-2 fusion. The complete mAb425 fusion genes were then cloned into the pHCMV vector for expression in eucaryotic cells.

Expression of Immunoconjugates

Introduction of vector constructs for the expression of a monovalent immunoconjugate including only the CH1 domain or divalent immunoconjugates including the CH2 and CH2 plus CH3 domains into host cells can be achieved e.g., by electroporation, DEAE dextran, calcium phosphate, Lipofectin or protoplast fusion. Any host cell type may be used provided that the recombinant DNA sequences encoding the immunoconjugate and the appropriate light chain are properly transcribed into mRNA in that cell type. Host cells may be, e.g., mouse myeloma cells which do not produce immunoglobulin such as Sp2/0-AG14 (ATCC CRL 1581), P3X63Ag8.653 (ATCC CRL 1580) or hamster cells such as CHO-K1 (ATCC CCL 61), or CHO/dhFr- (ATCC CRL 9096), or BHK-21 (ATCC CCL 10). For transient expression COS-1 (ATCC CRL 1650) or COS-7 (ATCC CRL 1651) may be used.

Transient Expression of Immunoconjugates

The expression vector pHCMV contains the origin of replication of the simian virus 40 (SV40). The cell line COS-7 is a derivative of the simian cell line CV-1 which has been transformed with an origin-defective SV40 virus. Therefore, plasmids containing the SV40 origin of replication will be amplified and the production of immunoconjugates will be improved. Supernatants were harvested 72 hours later and tested for EGF-receptor binding and cytokine concentration.

Permanent Expression of Immunoconjugates

Vectors containing recombinant constructs for the expression of immunoconjugates are introduced into apropriate host cells. The heavy and light chain constructs can be placed in the same or separate vectors: In the latter case both vectors may carry the identical selection marker such as Neomycin resistance or dhFr, or two different selection markers to select for the presence of both vectors. Selection for the dhFr marker can only be performed in dhFr negative cell lines such as CHO/dhFr-. Clones are analyzed for expression of immunoconjugates by EGF-receptor-specific ELISA. Selected clones are then further purified by limiting dilution cloning.

Construction of the Prokaryotic Expression Vectors for MAb425-CH1-cytokine Fusionprotein Expression The DNA sequences coding for the MAb425 light chain and the Fd fragment of the heavy chain have been introduced into the multiple cloning site of the pSW1 vector. The mature light chain coding sequence and mature heavy chain coding sequence are preceeded by the leader peptide of the bacterial pelB gene. The heavy chain coding sequence contains a 3' NcoI site. The cytokine encoding cDNAs were modified by PCR to introduce the NcoI (5' end) and the NotI (3' end) restriction sites. The cytokine genes were fused in frame directly to the CH1 domain of the heavy chain. Primers used in these experiments are summarized in Table II.

TABLE I

PCR primers used for the generation of MAb425-cytokine fusion proteins

| Construct | primer | primer DNA sequence |
|---|---|---|
| CH2-IL-2 | cγ1 5' primer* | 5'AACAGCTATGACCATG 3' |
| | cγ1 3' primer | 5'ACTTGAAGTAGGTGCCATTTTGGCTTTGGAGATGGT 3' |
| | cytokine 5' primer | 5'ATGGCACCTACTTCAAGT 3' |
| | cytokine 3' primer | 5'TATAGCGGCCGCGTCGACTCAAGTTAGTGTTGAGATG 3' |
| CH-3-IL-2 | cγ1 5' primer** | 5'CAAGACAAAGCCGCGGGAG 3' |
| | cγ1 3' primer | 5'ACTTGAAGTAGGTGCCATTTTACCCGGAGACAGGGAG 3' |
| | cytokine 5' primer | 5'ATGGCACCTACTTCAAGT 3' |
| | cytokine 3' primer | 5'CTTCTTCTAGACACTGCAG 3' |
| CH1-IL-4 | cytokine 5' primer | 5'ATCACCATGGTAATGCACAAGTGCGATATCACC 3' |
| | cytokine 3' primer*** | 5'CAGGAAACAGCTATGAC 3' |
| CH1-IL-7 | cytokine 5' primer | 5'CTTACCTGCCATGGATTG 3' |
| | cytokine 3' primer | 5'CAGAATTCGGATCCTTATCAGTG 3' |
| CH2-IL-7 | cγ1 5' primer* | 5'AACAGCTATGACCATG 3' |
| | cγ1 3' primer | 5'TTCGATATCACAATCCATTTTGGCTTTGGAGATGGT 3' |
| | cytokine 5' primer | 5'ATGGATTGTGATATCGAA 3' |
| | cytokine 3' primer | 5'TAATTCTAGATCAGTGTTCTTTAGTGC 3' |

TABLE II

PCR primers used for the generation of FAb425-cytokine fusion proteins (procaryotic expression)

| Construct | primer | primer DNA sequence |
|---|---|---|
| CH2-IL-2 | cytokine 5' primer | 5'CTTACCTGCCATGGCACCT 3' |
| | cytokine 3' primer | 5'TGGTAGCGGCCGCTTATCAAGTTAGTGTTGA 3' |
| CH1-IL-4 | cytokine 5' primer | 5'ATCACCATGGTAATGCACAAGTGCGATATCACC 3' |
| | cytokine 3' primer | 5'GGTAGCGGCCGCTTATCAGCTCGAACACTT 3' |
| CH1-IL-7 | cytokine 5' primer | 5'CTTACCTGCCATGGATTG 3' |
| | cytokine 3' primer | 5'TGGTAGCGGCCGCTTATCAGTGTTCTTTAGT 3' |

These vectors enable the efficient expression of functional Fab-cytokine fusion proteins in E. coli. The light chain and the heavy chain-cytokine fusion protein are located on a dicistronic messenger RNA placed under control of the inducible lac promotor (Skerra and Plückthun, Science 242: 1038–104, 1988). Therefore, expression of the Fab-fusion protein can be induced according to the requirements for culture conditions. The translation of both proteins from a dicistronic messenger RNA favours synthesis of equal amounts of Fd-IL-2 fusion protein and light chain thus increasing the chances for correct assembly into function Fab-fusion proteins. The two polypeptides are secreted into the periplasm of E. coli, where folding, formation of disulfide bonds and assembly into functional FAb425CH1 fusion protein takes place. Under prolonged culture of bacteria the proteins are excreted into the culture medium.

Expression of MAb425-CH1-IL-2 Fusion Protein in E. coli and Purification

E. coli strains suitable for protein expression were transformed with the expression plasmids. Cells were grown to $OD_{580}$ 0.5 and induced with IPTG (1 mM). Cells were grown overnight and supernatants and cells were harvested. The supernatant was applied to an antiMAb425 anti idiotypic column. The column was washed with phosphate buffered 0,5 M NaCl and bound proteins were eluted with 100 mM Glycine 0,5 M NaCl, pH 2,5. The eluate was immediately neutralized with Tris 2.5 M pH8. MAb425-CH1-IL-2-containing fractions were pooled, concentrated and dialyzed against PBS.

Binding Properties of MAb425 Immunoconjugates

The binding properties of the MAb425 immunoconjugates were determined by EGF-receptor-specific ELISA. In brief,microtiter plates were coated over night at 4° C. with purified EGF-receptor and washed to remove unbound protein. The plates were incubated with fusion protein-containing supernatants or supernatants containing unconjugated MAb or Fab fragments or the proteins in purified form. Plates were washed and incubated with goat-anti-human IgG and IgM (heavy and light chain) conjugated to peroxidase. Substrate was added and the amount of bound EGF-receptor-specific protein was determined by measure at 450 nm (FIG. 2). The cytokine concentration was determined by commercially available ELISAs specific for each cytokine according to the manufacturers instructions (data not shown).

Proliferation of Leukocytes

Tumor-Specific Effector Cells

Peripheral blood mononuclear leukocytes and tumor infiltrating lymphocytes (TILS) isolated from melanoma patients were co-cultured with irradiated (30Gy) autologous tumor cells in medium (RPMI 1640, 1% Penicillin/Streptomycin, 1% Glutamin, 20 mM Hepes, 50 mM β Mercaptoethanol, 10% fetal calf serum, 20 U/ml IL-2, 20 U/ml IL-4). Responder cells were weekly stimulated with autologous tumor cells.

Determination of Proliferation

Figure 4:
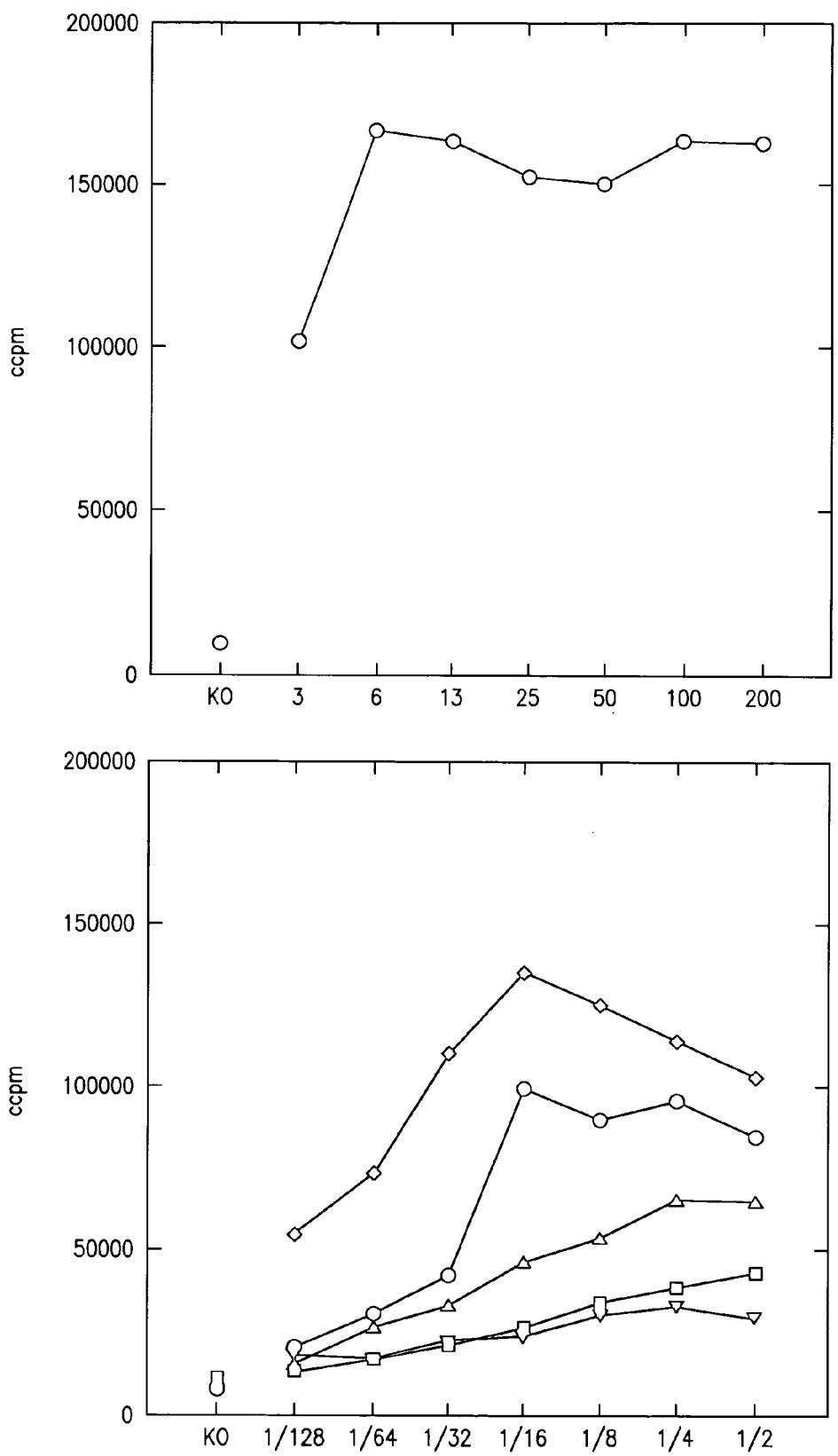
Figure 5:
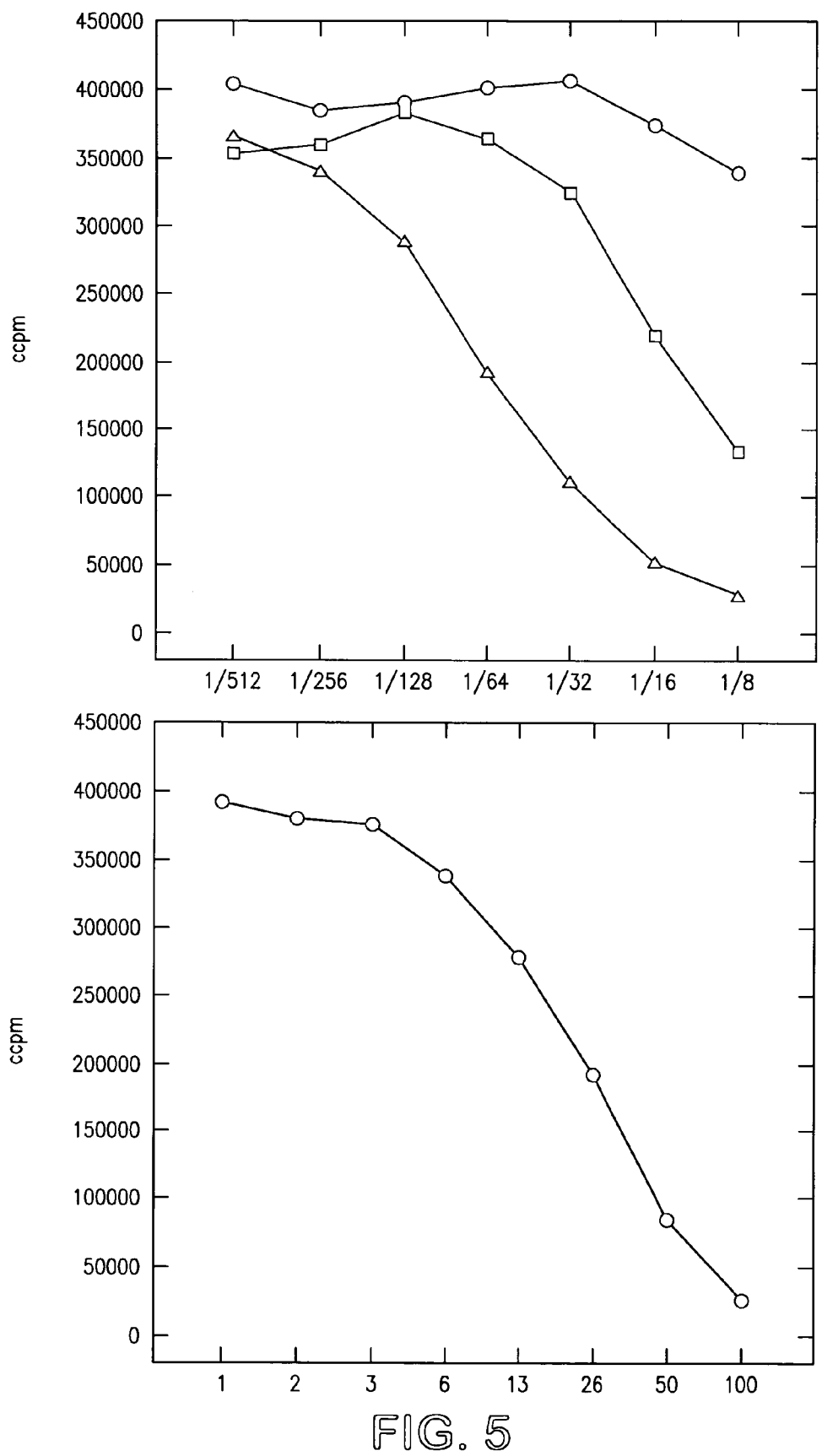

The cytokine-mediated proliferation may be determined with
a) appropriate indicator cell lines. In the case of IL-2 the IL-2-dependent mouse cell line CTLL-2 (ATCC TIB 241) (FIG. 3A) or other IL-2-dependent cell lines may be used.
b) in vitro expanded tumor infiltrating lymphocytes (FIG. 3B)
c) freshly isolated blood mononuclear cells pretreated with PHA-M (Sigma). In this case the experiment was done with MAb425-IL4 fusion proteins (FIG. 4).

Freshly prepared human peripheral blood leukocytes from healthy blood donors or melanoma patients or TILs isolated from melanoma patients were propagated in vitro (see above). For assaying the fusion proteins the lymphocytes were cultured in 96 well flat-bottom microtiter plates at a density of $1 \times 10^5$ cells per well in a final volume of 200 μl. Cells were incubated with fusion protein-containing supernatants or supernatants containing unconjugated MAb or supernatants containing unconjugated cytokines or the proteins in purified form. After 72 hours the cells were pulsed with 0.5 μCi $^3$H-thymidine. Incorporation of radioactivity was determined after overnight incubation by liquid scintillation β-plate counting. The results are expressed as the average cpm.

Determination of Cytotoxicity of MAb425-TNFα Immunoconjugates

Determination of TNFα-Mediated Cytotoxicity

TNFα was described to be directly cytotoxic for certain cells, including a variety of tumor cells. The direct cytotoxic potential of TNFα can be determined with L929 murine fibroblasts (ATCC CCL 1) or WEHI 164 (ATCC CRL 1751) or other TNFα-sensitive cell lines as described (Flick & Gifford, 1984, J. Immunol. Meth. 68:167). In FIG. 4 the the cytotoxic potential of MAb425CH1-TNFa and MAb425CH2-TNFα are demonstrated on WEHI164 cells as indicator cell line.

Determination of $TNF_d$-Induced Cytotoxicity

EGF-receptor-positive cell lines such as the highly invasive and spontaneously metastatic, EGF-receptor-positive cell line C8161 (Welch et al., 1991, Int. J. Cancer 47:227, and references cites therein) may be used as target cells for cytolysis by allogeneic tumor infiltrating lymphocytes or freshly isolated human peripheral blood lymphocytes from melanoma patients or healthy donors. Culture conditions for tumor cells and TILs have been described previously (Shimizu et al., 1991, Cancer Res. 51:6153); the skilled worker would know from such publications the conditions effective to induce lysis with an immunoconjugate according to the present invention.

In vitro cytotoxicity assays were performed using $^{51}$Cr-labeled tumor target cells. Target cells were labeled with $^{51}$Cr(100 μCi/$10^7$ cells) for 1 hour followed by three washing steps to remove excessive $^{51}$Cr. $2 \times 10^3$ target cells per well were co-incubated with effector cells in 96 well microtiter plates in the presence of fusion protein-containing supernatants or supernatants containing unconjugated MAb or supernatants containing unconjugated cytokines (controls) or the proteins in purified form. The supernatants or purified proteins were serially diluted in culture medium and assayed in triplicates. The plates were incubated for 4 hours at 370° C. in a 10% $CO_2$ atmosphere. The cells were then removed by centrifugation and radioactivity in the supernatants was determined in a γ counter. Percent specific $^{51}$Cr-release was calculated according to the formula:

$$\% \text{ specific } ^{51}\text{Cr-release} = 100 \times \frac{(\text{Experimental release} - \text{spontaneous release})}{(\text{maximum release} - \text{spontaneous release})}$$

Therapeutic use of the Immunoconjugates

The immunoconjugates according to the invention can be administered to human patients for therapy. Therefore, it is an object of the invention to provide a pharmaceutical formulation comprising as active ingredient at least one fusion protein defined above and in the claims, associated with one or more pharmaceutically acceptable carrier, excipient or diluent therefore.

Typically the immunoconjugates of this invention will be injected intravenously or parenterally. Generally, the dosage ranges for the administration of the immunoconjugates are large enough to produce the desired tumor suppressing and tumor lysing effect. The dosage will depend on age, condition, sex and extent of the desease in the patient and can vary from 0.1 mg/kg to 200 mg/kg, preferrably from 0.1 mg/kg to 100 mg/kg/dose in one or more doses administrations daily, for one or several days. These can be determined routinely, according to standard procedures.

Preparations for parenteral administration includes sterile aqueous or non-aqueous solutions, suspensions, and emulsions. Examples of non-aqueous solvents are propylene glycol, polyethylene glycol, vegetable oils such as olive oils and injectable organic esters such as ethyl oleate and other solvents known in the art which are suitable for these purposes. The immunoconjugates of this invention can be used in a composition comprising a physiologically acceptable carrier. Examples of such suitable carriers are saline, PBS, Ringer's solution, or lactated Ringer's solution. Preservatives and other additives such as antibiotics, antioxidants, and chelating agents may also be present in the pharmaceutical formulations.

The pharmaceutical formulations of the present invention are suitable for the treatment of all kinds of tumors, including melanomas, gliomas and carcinomas, as well as blood tumors and solid tumors.

The entire disclosures of all applications, patents and publications, cited above and below, and of corresponding application(s) EP 93120865.6, filed Dec. 24, 1993, are hereby incorporated by reference.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A fusion protein which is MAb 425-CH2-TNFα, MAb 425-CH3-TNFα, Mab 425-CH2-IL2, or MAb 425-CH3-IL2.

2. A pharmaceutical composition comprising a fusion protein according to claim 1 and a physiologically acceptable carrier.

3. The fusion protein of claim 1 which is MAb 425-CH2-TNFα, or MAb 425-CH3-TNFα.

* * * * *